United States Patent [19]

Williford

[11] Patent Number: 4,860,589

[45] Date of Patent: Aug. 29, 1989

[54] PROCEDURE FOR ESTIMATING FRACTURE ENERGY FROM FRACTURE SURFACE ROUGHNESS

[75] Inventor: Ralph E. Williford, Kennewick, Wash.

[73] Assignee: Battelle Memorial Institute, Richland, Wash.

[21] Appl. No.: 130,869

[22] Filed: Dec. 10, 1987

[51] Int. Cl.[4] ............................................. G01N 19/08
[52] U.S. Cl. ........................................... 73/799; 73/105
[58] Field of Search .................. 73/799, 87, 105, 804, 73/810, 834, 845, 851

[56] References Cited

U.S. PATENT DOCUMENTS 4,299,120 11/1981 Barker ....................................... 73/87

Primary Examiner—Jerry W. Myracle
Attorney, Agent, or Firm—Joseph J. Hauth; Robert Keith Sharp

[57] ABSTRACT

The fracture energy of a material is determined by first measuring the length of a profile of a section through a fractured surface of the material taken on a plane perpendicular to the mean plane of that surface, then determining the fractal dimensionality of the surface. From this, the yield strength of the material, and the Young's Modulus of that material, the fracture energy is calculated.

2 Claims, 1 Drawing Sheet

PROCEDURE FOR ESTIMATING FRACTURE ENERGY FROM FRACTURE SURFACE ROUGHNESS

This invention was made with U.S. Government support and the Government has certain rights therein, under Contract No. F49620-87-C-0031 (Battelle Northwest Contract No. 2311107367).

This invention relates to a method for determining the fracture energy of material. It is defined as the energy per unit area required to fracture a given material. It may be expressed in, for example, joules per square centimeter or foot-pounds per square inch.

SUMMARY OF THE INVENTION

A technique is described whereby the fracture energy (or fracture toughness) can be estimated from measurements of the roughness of the fracture surface itself. This procedure provides a significant cost savings for the fracture analysis of nonremovable or contaminated materials or structures.

DETAILED DESCRIPTION

Figure 1:
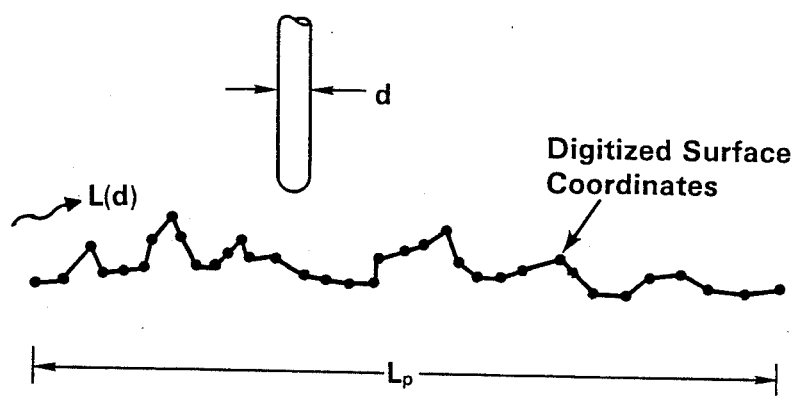
FIG. 1 is a graph used to explain one step of the method of this invention.
Figure 2:
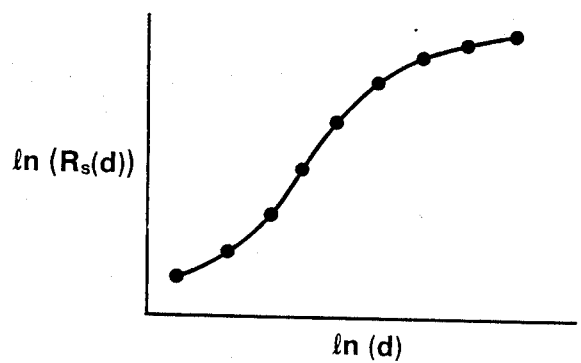
FIG. 2 is a graph further illustrating another step.

The procedure consists of six major steps, as follows:

1. Access to the fracture surfaces must be obtained. This generally requires that the specimen be completely fractured into two parts.
2. Cleaning and replication of the exposed fracture surface are then performed using the methods of the ASM Handbood (Vol. 9, pp. 56-60). This is essentially a repetitive process whereby the first replicates taken using, for example, softened acetate sheets, serve as cleaning steps. The sheets are applied successively until one comes off clean. The next is hardened and used in the subsequent steps.
3. The replicate is then taken to the metallurgical laboratory and sectioned on a plane perpendicular to the mean plane of the fracture surface. The cut face is subsequently polished to produce a clear profile of the fracture surface at the desired location.
4. The coordinates of the fracture surface profile replica are then measured and recorded. This can be performed in a two-stage process using high-resolution photography and a computer digitizer to record the detailed profile coordinates, or more advanced metallographic equipment such as a Zeiss Videoplan.
5. Having recorded the detailed measurements of the fracture surface profile as above, the fractal dimensionality of the surface ($D_s$) is computed as follows. The high-resolution coordinates of the rough and irregular profile are used to compute the total length of the profile as if this length was measured by traversing the surface by a stylus tip of diameter d. d is larger than the minimum difference between digitized surface coordinates (see FIG. 1). The resulting total length is designated L(d), and is divided by the projected length $L_p$ to give the profile roughness parameter $R_L(d) = L(d)/L_p$. Then the surface roughness parameter $R_s(d)$ is computed according to $R_s(d) = 4/\pi[R_L(d) - 1]$. This calculation is performed for a succession of increasingly larger d values, and the result can be plotted as in FIG. 2. A constant K is chosen so that the equation $$D_s = 2 - \frac{\ln[R_S(d)/K]}{\ln(d)}$$

provides a statistical best fit to the data in FIG. 2; ln is the natural logarithm. This determines $D_s$.

6. The above value for $D_s$ is then substituted into the equation $J_{IC} = CL^{(D_s - 2)}$, where $J_{IC}$ is the fracture energy, C is a constant (see below) and L is the scale of observation. L is best approximated by the observed crack growth increment. This is particularly easy for cases of fatigue, where the growth increment is the distance between fatigue striations. C is equal to $\pi S_Y^2/E$ for brittle fracture, and C equals $\pi S_Y^2 a/E$ for ductile fractures (Williford, 1987). $S_Y$ is the material yield strength, E is its Young's Modulus, and a is the crack length. This produces an estimate for the fracture energy $J_{IC}$, from which the toughness $K_{IC}$ can be easily computed, by the equation $$K_{IC} = \sqrt{J_{IC}E} \ .$$

For a detailed mathematical development, see: Williford, R. E. 1987. "A Similarity Analysis of Fracture." BN-SA-2554, Battelle Northwest Laboratories, Richland WA, published at pages 39-44, Proceedings of the December 1987 Winter Annual Meeting, ASME, and in Damage Mechanisms in Composite Materials AD 12, Edited by A. F. D. Wayne and J. G. Haritos (ASME, 1987).

I claim as my invention:

1. A method of determining the fracture energy of a piece of material having a fractured surface comprising measuring the length of the profile of a section through said fracture surface taken on a plane perpendicular to the mean plane of said fractured surface, determining therefrom the fractal dimensionality of the surface and determining the fracture energy from said fractal dimensionality, the yield strength of said material and Young's Modulus of said material.

2. A method as defined in claim 1 wherein said steps of measuring the length of said profile comprises forming a replica of said surface and cutting said replica on a plane perpendicular to the mean plane of said fracture surface.

* * * * *